US006959108B1

(12) United States Patent
Bartelt et al.

(10) Patent No.: US 6,959,108 B1
(45) Date of Patent: Oct. 25, 2005

(54) IMAGE BASED DEFECT DETECTION SYSTEM

(75) Inventors: Todd F. Bartelt, Lenexa, KS (US); Richard A. Sizemore, Lenexa, KS (US); Robert E. Larson, Overland Park, KS (US)

(73) Assignee: Interactive Design, Inc., Lenexa, KS (US)

( * ) Notice: Subject to any disclaimer, the term of this patent is extended or adjusted under 35 U.S.C. 154(b) by 760 days.

(21) Appl. No.: 10/010,712

(22) Filed: Dec. 6, 2001

(51) Int. Cl.[7] ............................. G06K 9/00; H04N 9/47
(52) U.S. Cl. ...................... 382/141; 348/92; 348/125; 348/127; 356/237.1; 356/428; 250/306; 700/110
(58) Field of Search ............ 382/141–152; 348/86–92, 348/125–134; 356/237.1–237.642, 426–431; 250/306–311, 250/223 B; 700/95–212; 29/833; 438/16

(56) References Cited

U.S. PATENT DOCUMENTS

| | | | |
|---|---|---|---|
| 5,026,982 A * | 6/1991 | Stroman ................. 250/223 R |
| 5,153,668 A | 10/1992 | Katzir et al. | |
| 5,184,732 A * | 2/1993 | Ditchburn et al. .......... 209/576 |
| 5,351,078 A | 9/1994 | Lemelson | |
| 5,434,616 A * | 7/1995 | Anger et al. ................... 348/92 |
| 5,499,055 A * | 3/1996 | Anger et al. ................... 348/92 |
| 5,591,462 A | 1/1997 | Darling et al. | |
| 5,748,324 A * | 5/1998 | Howarth et al. ............ 356/425 |
| 5,898,169 A * | 4/1999 | Nordbryhn .............. 250/223 B |
| 5,957,306 A | 9/1999 | Hoffman | |
| 6,205,237 B1 * | 3/2001 | Focke et al. ................ 382/141 |
| 6,255,683 B1 * | 7/2001 | Radens et al. .............. 209/576 |

* cited by examiner

Primary Examiner—Bhavesh M. Mehta
Assistant Examiner—Aaron Carter
(74) Attorney, Agent, or Firm—Shughart Thomson & Kilroy PC

(57) ABSTRACT

In an inspection system, workpieces to be inspected are consecutively and automatically launched to pass unsupported through the field of view of a plurality of cameras. As a workpiece passes through the field of view of the cameras, a sensor is activated which communicates with a computer system to activate the cameras to capture an unobstructed image, or image data, of the workpiece. The image data is then analyzed by a computer program to verify whether the image data indicates that the workpiece does not meet established criteria and therefore is considered defective. If the image does not meet the established criteria, the workpiece is rejected and segregated from workpieces which have not been identified as defective.

18 Claims, 11 Drawing Sheets

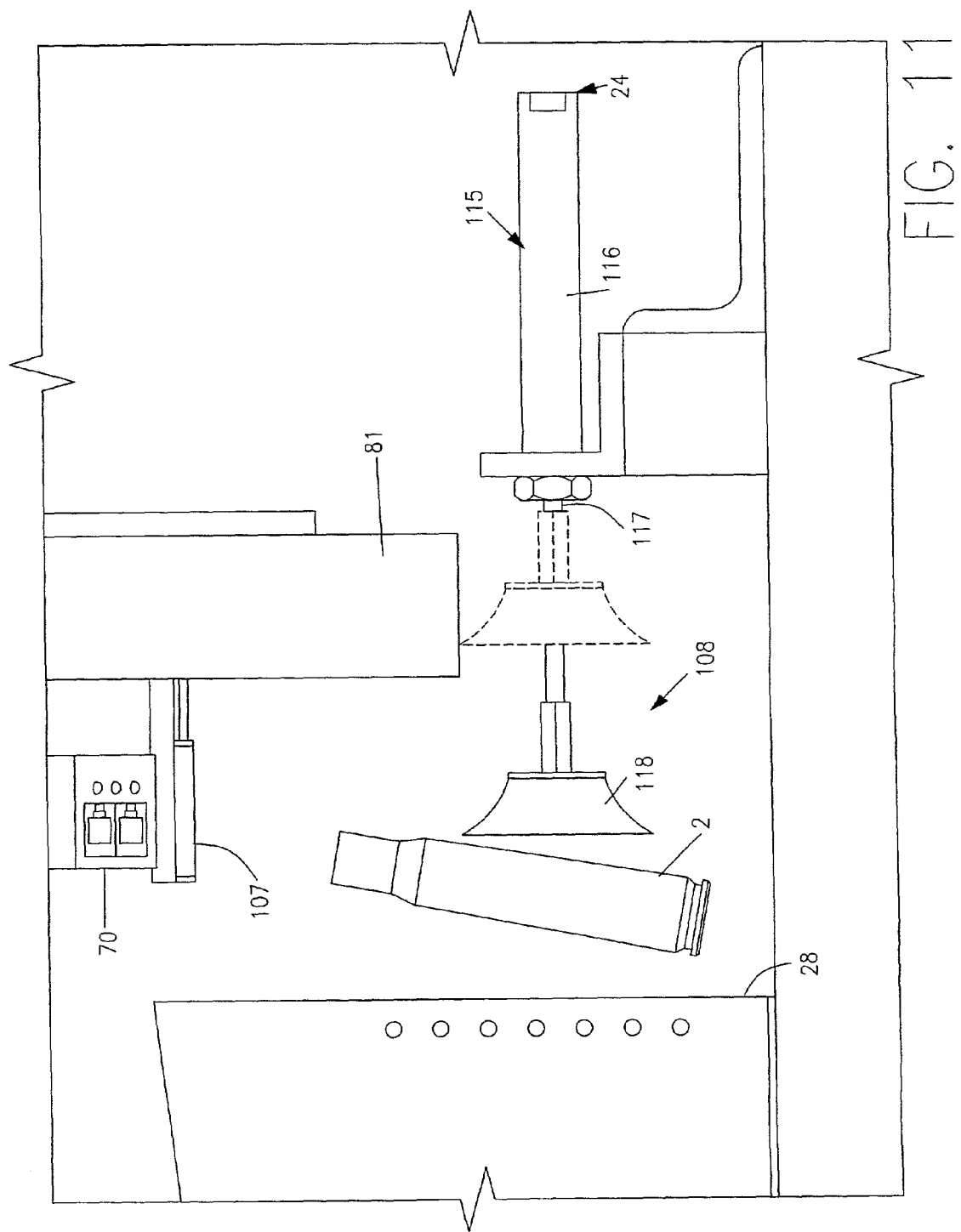

IMAGE BASED DEFECT DETECTION SYSTEM

BACKGROUND OF THE INVENTION

1. Field of the Invention

This invention relates to a system for inspecting a workpiece in a high speed, automated workpiece inspection process.

2. Background

Automated systems to optically inspect workpieces and detect defects in the workpieces have been developed to improve the quality of manufactured goods. The workpieces to be inspected are typically supported on a conveyor and conveyed past a light source and one or more cameras which capture a visual image of each workpiece. The visual images are then analyzed using a computer program. Existing software can compare the image of the workpiece versus a standardized image and make a determination of whether the workpiece meets product specifications or contains defects. Software also exists which can be used to measure various features of the captured image of the workpiece and compare the measurements versus established standards to determine if the product meets specifications or contains defects. If the analysis determines a defect is present, it is known to automatically remove the defective item from the product stream.

A significant limitation of currently available optical inspection systems is that because the workpiece is supported on a conveyor during the inspection process, it is difficult to inspect all of the surfaces of the workpiece which need to be inspected at one station or through one pass. Systems have been developed to maneuver or rotate the workpiece as it passes through an inspection station, but such systems are unnecessarily complicated and expensive and are not amenable for use in high volume manufacturing processes in which a large number of workpieces must be produced and inspected in a short amount of time to maintain manufacturing efficiencies.

There remains a need for a system and apparatus which facilitates the automatic image based inspection of a workpiece which provides an unobstructed view of the workpiece.

SUMMARY OF THE INVENTION

In the inspection system of the present invention, the workpieces to be inspected are consecutively released or launched to pass unsupported through the field of view of one or more cameras. As a workpiece passes through the field of view of a camera, a sensor is activated which communicates with a computer system to activate the camera to capture an image, or image data, of the workpiece. The image data is then analyzed by a computer program to verify whether the recorded image meets established criteria. If the image does not meet the established criteria, the workpiece is rejected.

In one embodiment the workpiece is dropped through a space onto which a plurality of cameras are focused to obtain a circumferential view of the workpiece. Upon tripping of the sensor, the cameras simultaneously capture an image of the workpiece. Additional cameras may be positioned and activated in response to tripping of the sensor to simultaneously obtain views looking up or down at the workpiece.

A light source may also be provided to shine light onto or into the workpiece upon activation of the sensor. It is particularly useful to shine light into a hollow workpiece when inspecting the hollow item for holes or openings in its walls. The cameras then record or detect light emitted through any holes in the hollow workpiece. The pattern of light captured by the camera can then be analyzed by computer software to identify defects.

BRIEF DESCRIPTION OF THE DRAWINGS

FIG. 11 is a greatly enlarged and fragmentary view similar to FIG. 3 showing an abutment member of a workpiece diverter extended to divert a shell casing into a defective product chute and showing the abutment member retracted in phantom lines.

DETAILED DESCRIPTION OF THE INVENTION

Figure 1:
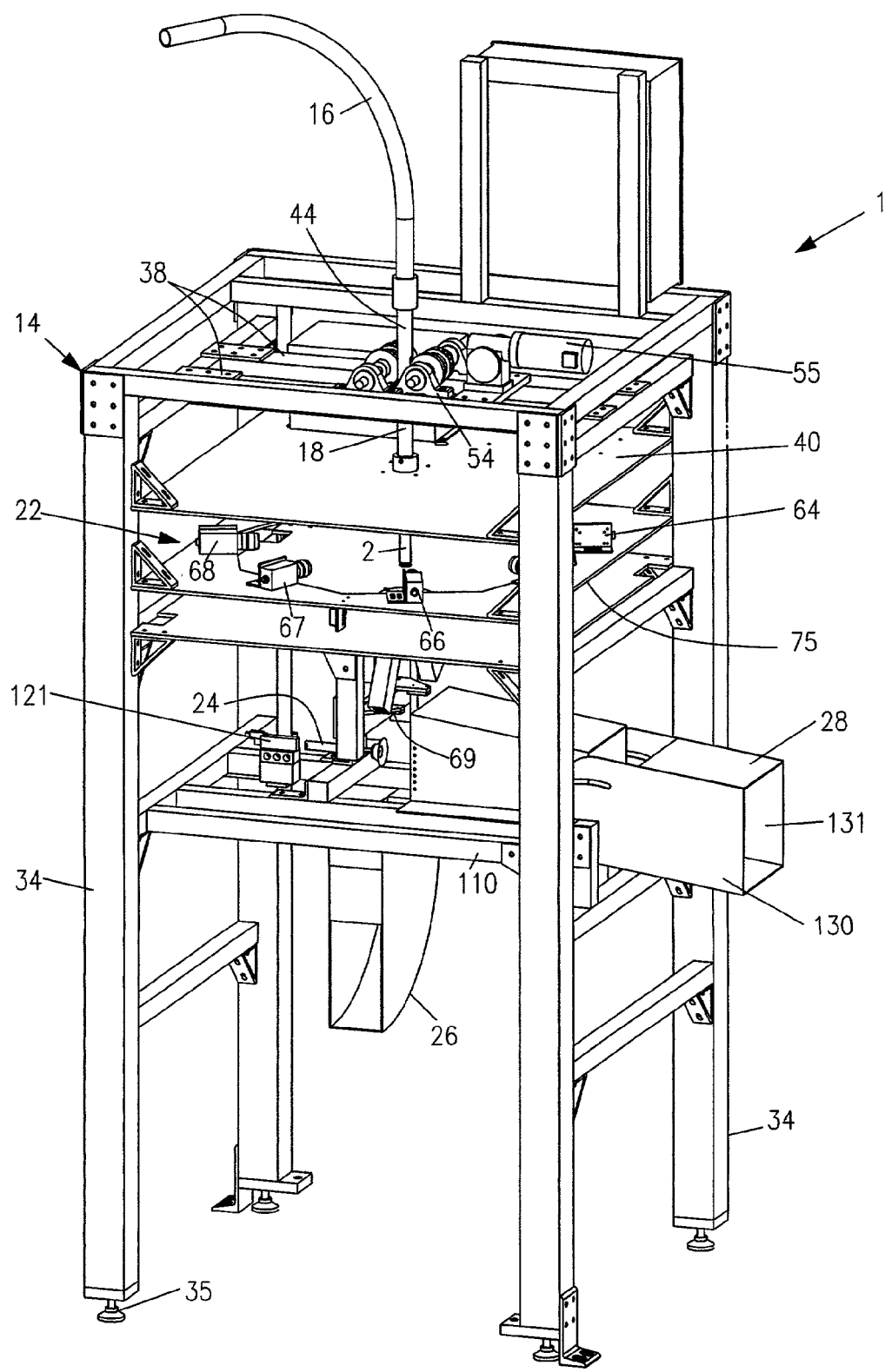
FIG. 1 is a perspective view of an automated image based workpiece inspection apparatus adapted for inspecting shell casings.

As required, detailed embodiments of the present invention are disclosed herein; however, it is to be understood that the disclosed embodiments are merely exemplary of the invention, which may be embodied in various forms. Therefore, specific structural, functional and procedural details disclosed herein are not to be interpreted as limiting, but merely as a basis for the claims and as a representative basis for teaching one skilled in the art to variously employ the present invention in virtually any appropriately detailed structure.

The inspection system of the present invention is adapted for the consecutive inspection of identical goods such as in a manufacturing or assembly process. The system is particularly well suited for identifying any defects in hollow items including tubes, cans, casings, bottles and the like. Referring to the drawings in more detail, and initially to FIGS. 1 through 3, the reference numeral 1 refers to an inspection apparatus which embodies the present invention.

Figure 4:
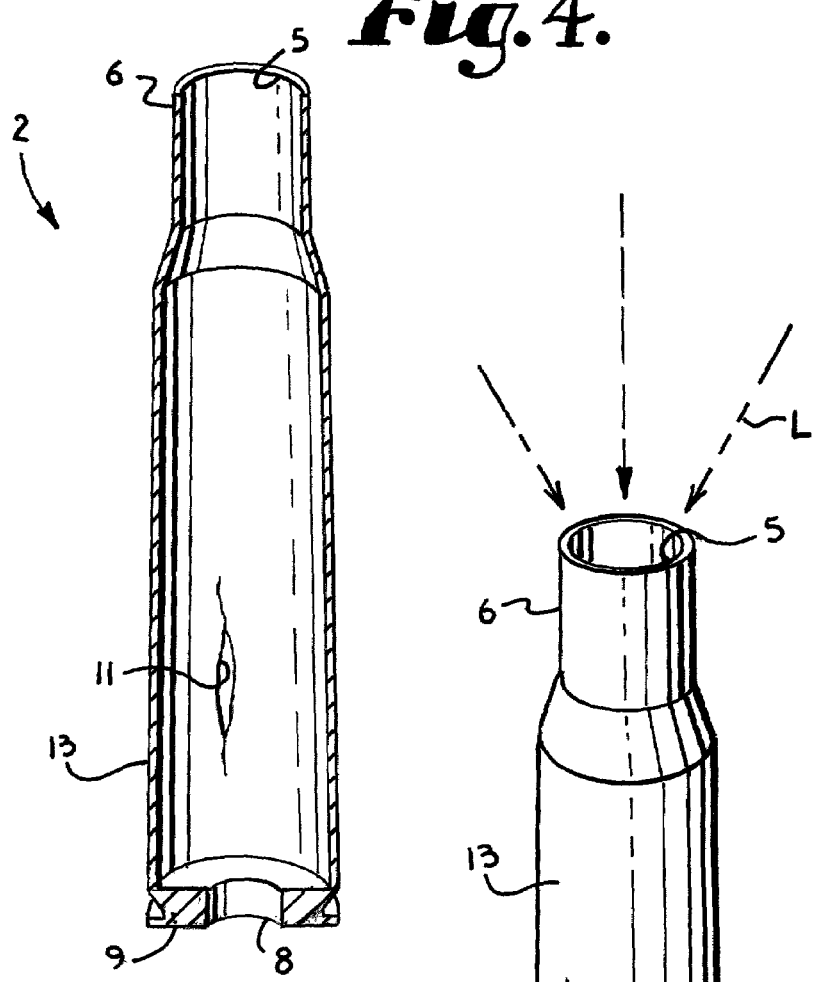
FIG. 4 is a cross-sectional perspective view of a shell casing having a defect formed therein.

The inspection apparatus 1 will be described with reference to its use in inspecting ammunition shell casings, such as shell casing 2 shown in cross-section in FIG. 4. As used herein, shell casings 2 may also be referred to as workpieces 2, the term workpiece generally referring to an item to be inspected using the inspection apparatus 1.

Shell casing 2 is representative of a shell casing for a 50 caliber round of ammunition. Metal shell casings are generally formed from metal blanks using various metal forming precesses including stamping and drawing of the metal. The casing 2 is formed to include a first opening or mouth 5 at its tip 6 and a second, smaller opening or primer flash opening 8 in its base 9. The primer flash opening or primer opening 8 is adapted to receive a primer (not shown), after which the casing 2 may be filled with powder through mouth 5. Shell casings can be formed from materials other than metal; for example, shotgun shell casings typically include a metal base connected to a plastic or heavy paper sleeve.

During the process of forming a shell casing 2, unwanted cracks, splits, holes and other openings, such as hole 11 can be formed in the casing 2, generally in the circumferential wall 13 thereof. Not all openings are large enough to result in the casing being deemed defective. For example, openings that are narrower than the width of individual grains of powder may not cause a casing to be considered defective. Product specifications are typically established to determine the size of an opening which will result in the casing being considered defective.

The inspection apparatus 1 may be installed in a production line for the workpieces to be inspected. Workpieces to be inspected may be fed into the inspection apparatus 1 continuously in a product stream from the manufacturing process, or it is foreseen that accumulated batches of workpieces could be regularly fed into the inspection apparatus 1.

Figure 2:
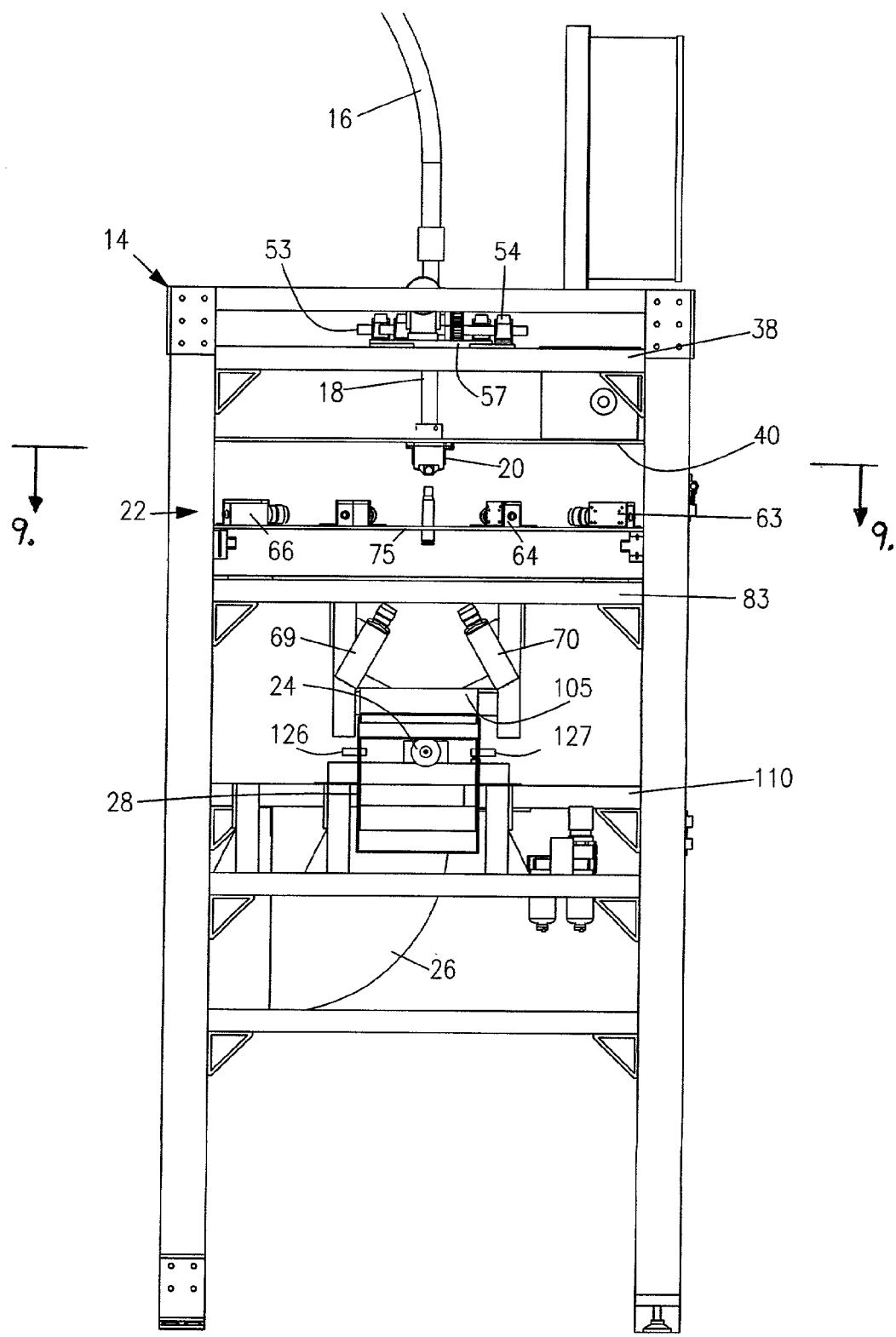
FIG. 2 is a right side elevational view of the inspection apparatus.
Figure 3:
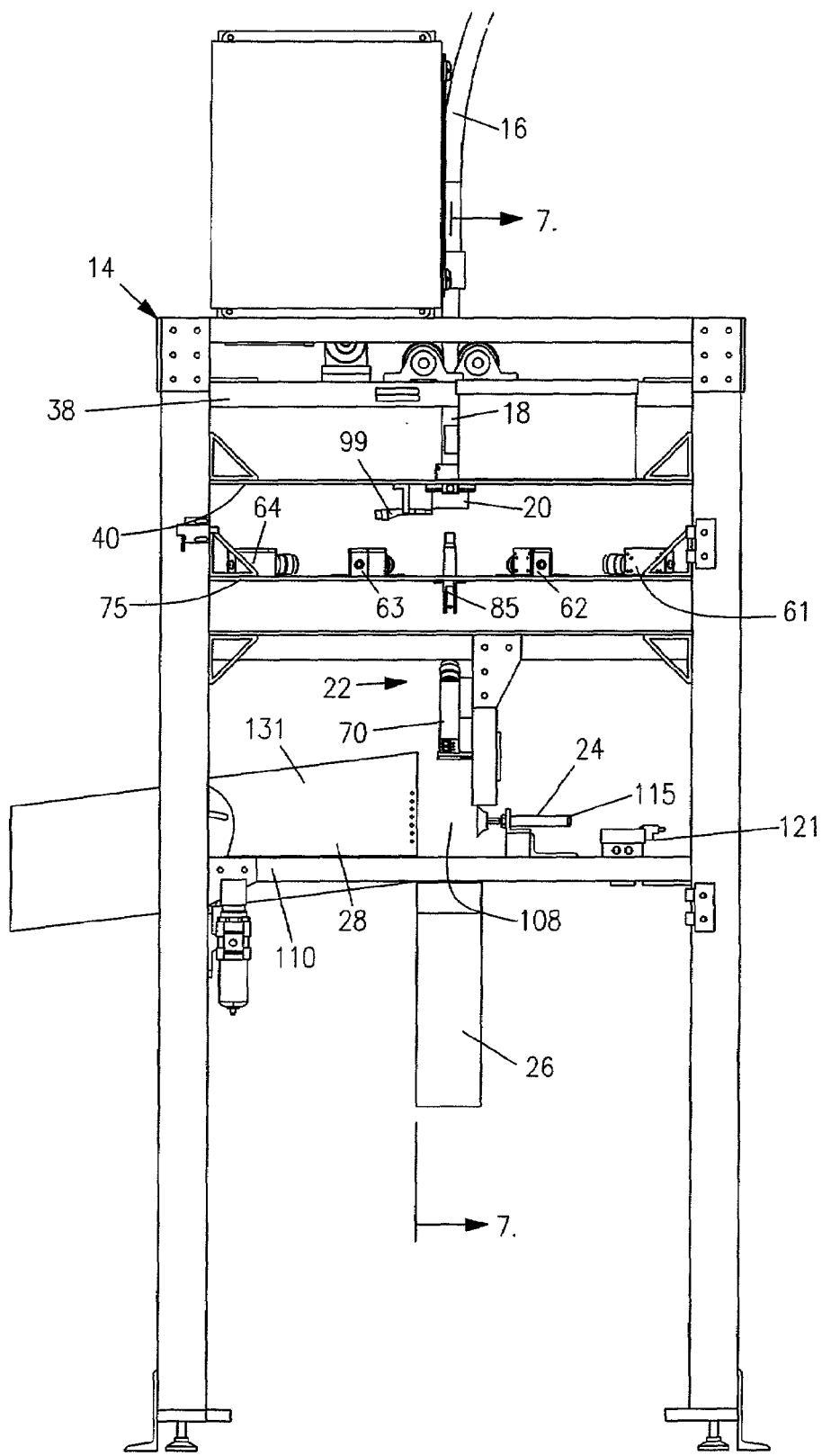
FIG. 3 is a rear elevational view of the inspection apparatus.
Figure 5:
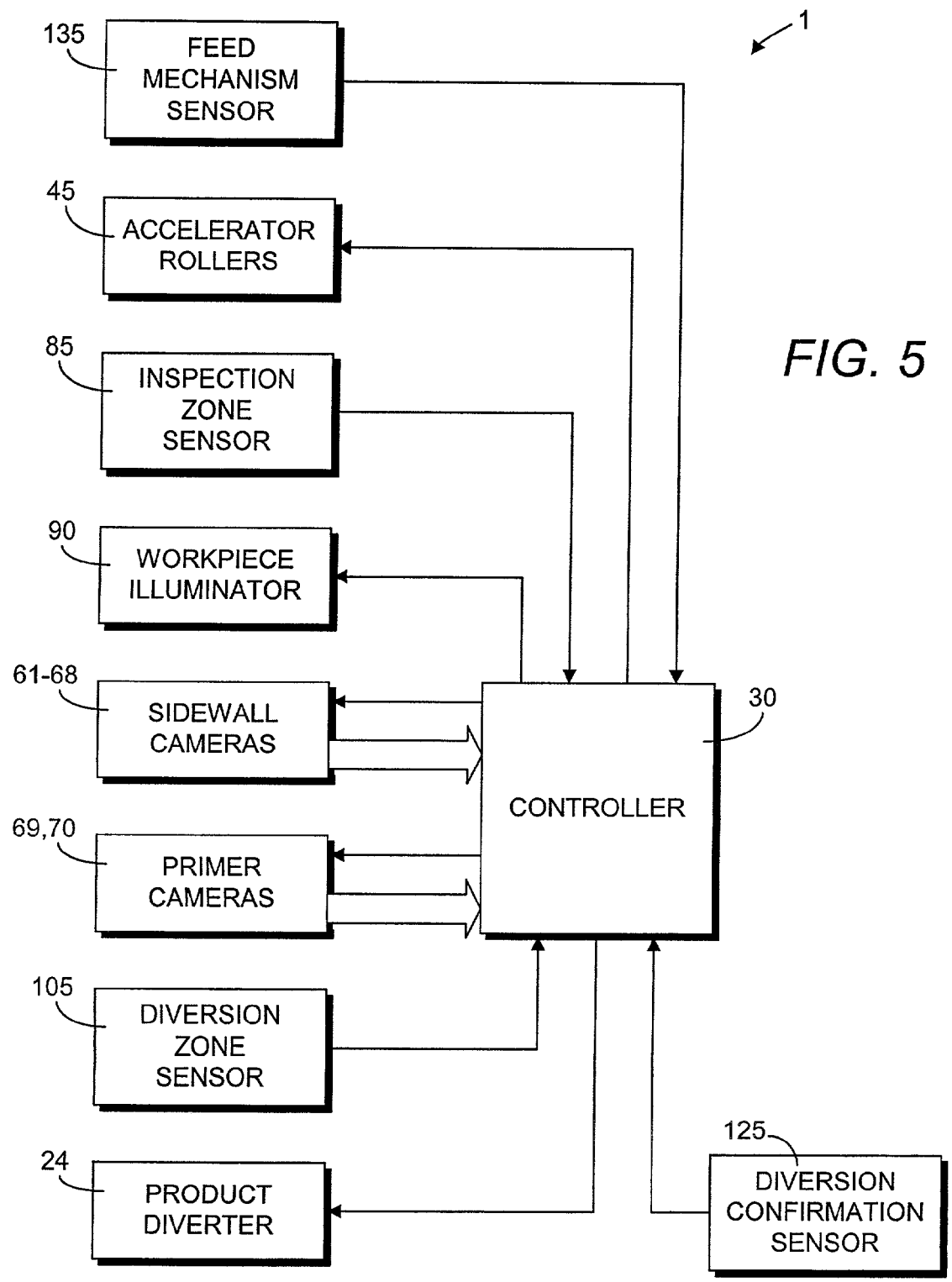
FIG. 5 is a schematic diagram of the control system of the inspection apparatus.

Referring to FIGS. 1–3, the inspection apparatus 1 includes a frame 14, a workpiece feed tube 16, a launch assembly 18, an illumination assembly 20, an image capturing assembly 22, a product diverter 24, an acceptable product chute 26, and a defective product chute 28. The inspection apparatus also includes a controller or computer system 30, shown diagrammatically in FIG. 5, on which one or more computer programs are run to control operation of various components of the apparatus 1 and analyze image data collected by the image capturing assembly 20. It is to be noted that except as shown in FIG. 5, electrical connections, fiber optic cable, pneumatic hoses and other power and communication links generally are not shown in the drawings.

As best seen in FIG. 1, the frame 14 includes four primary support legs 34 each with a height adjustable foot 35. Additional frame members and support panels are provided to support the functional components of the inspection apparatus as described hereafter.

Figure 6:
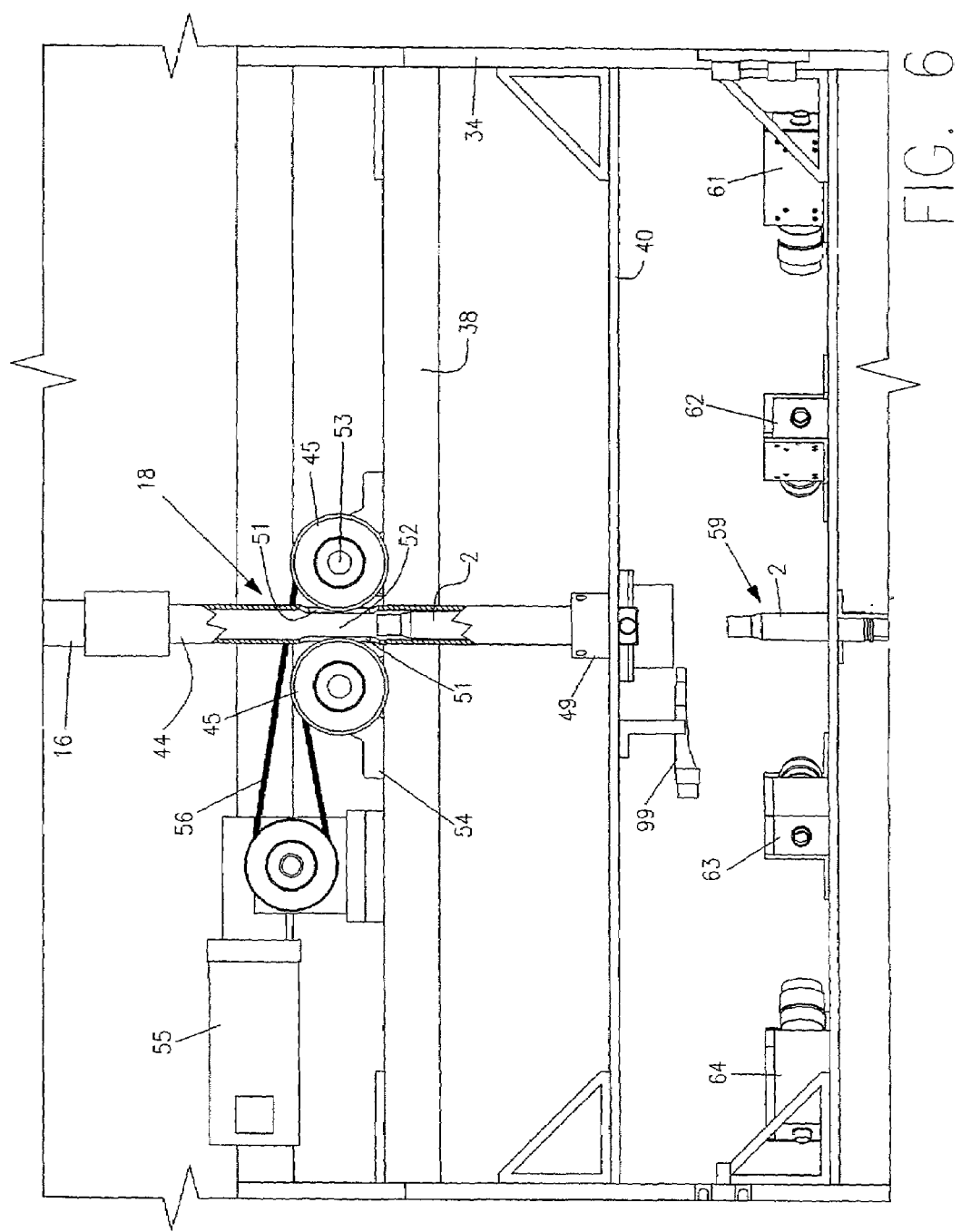
FIG. 6 is an enlarged and fragmentary view of the inspection apparatus as shown in FIG. 3 with portions broke away to show interior detail of a launching tube used to launch a shell casing to be inspected.
Figure 7:
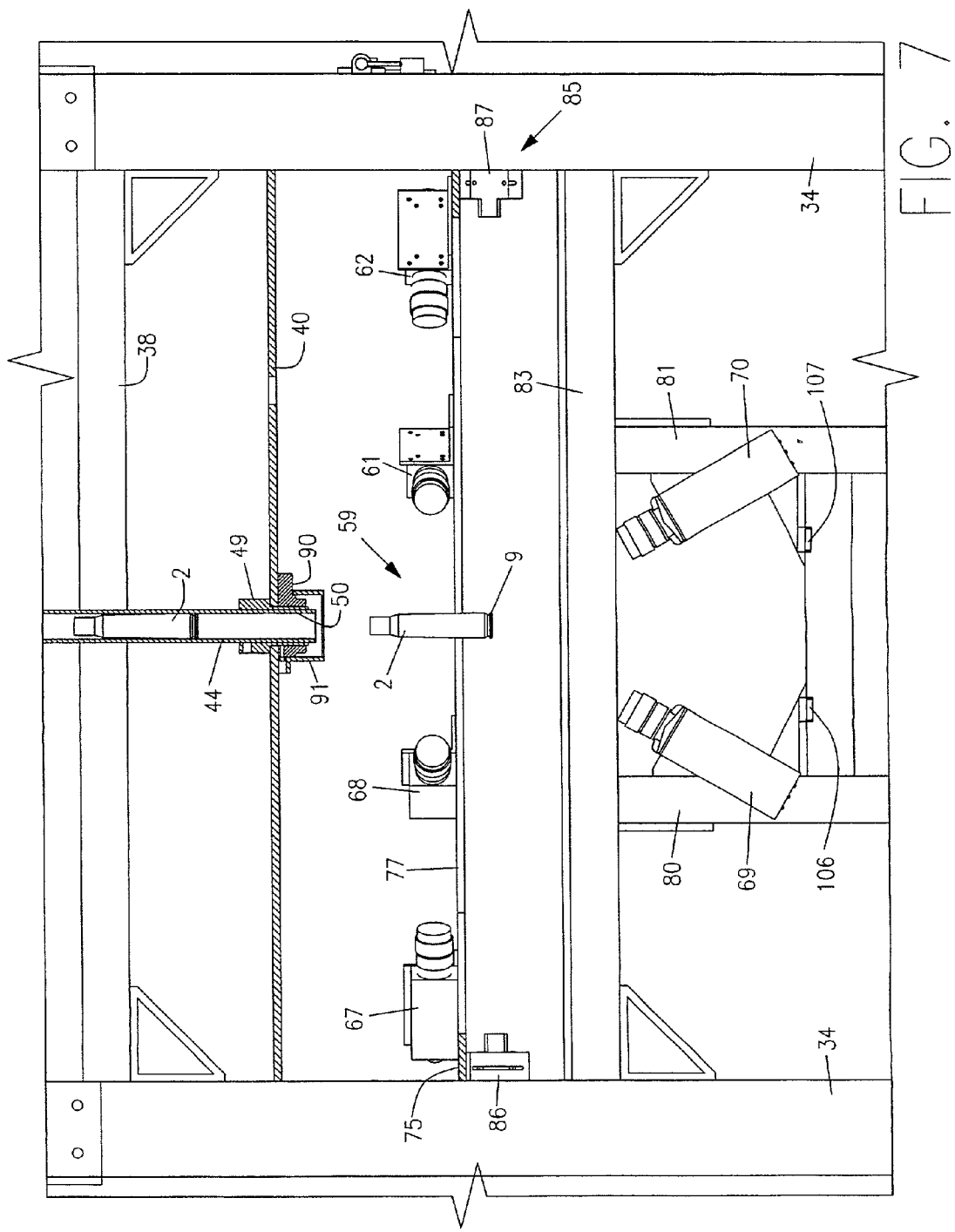
FIG. 7 is an enlarged and fragmentary, cross-sectional view of the inspection apparatus taken generally along line 7—7 of FIG. 3.
Figure 8:
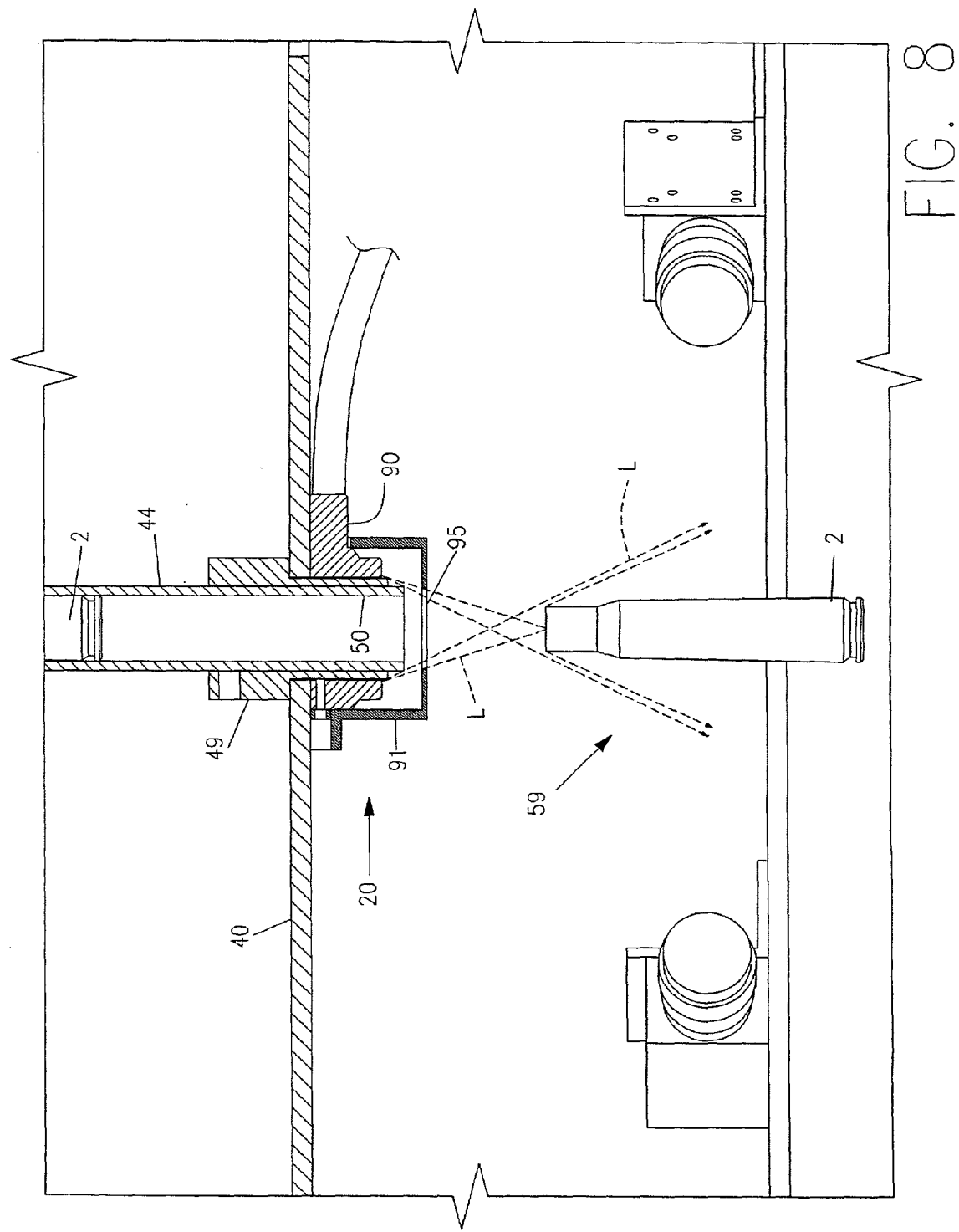
FIG. 8 is a greatly enlarged view similar to FIG. 7 showing light being emitted from a ring light and directed into the shell casing.

The launch assembly 18, as best seen in FIGS. 6–8, is supported on upper frame members 38 and upper support plate 40 which are in turn connected to the support legs 34. The launch assembly 18 generally comprises a launch tube 44 and a pair of accelerator rollers 45. The workpiece feed tube 16 is connected to an upper end of the launch tube 44 and feeds workpieces successively into the launch tube 44. The workpieces can be fed into the feed tube 16 by means such as a centrifugal feeder (not shown) or other known means which are adapted to feed the casings 2 into the feed tube 16 in a particular orientation, such as base first.

The launch tube 44 is mounted in vertical alignment with an upper portion extending between upper frame members 38 and a lower end extending through a hole in the upper support plate 40 as shown in FIG. 7. A flanged collar 49 connected to and extending around the launch tube 44 proximate a lower end thereof supports the launch tube 44 on the upper support plate 40. A short lower section 50 of the launch tube 44 extends below the upper support plate 40. The inner diameter of the launch tube 44 is slightly wider than the outer diameter of a workpiece or shell casing 2 to permit it to slide through the launch tube 44. Referring to FIG. 6 a pair of roller receiving slots 51 are formed on opposite sides of the launch tube in the portion extending above the upper frame members 38. The accelerator rollers 45 are mounted to the frame 14 so that a portion of the outer periphery of each roller 45 extends through a respective roller receiving slot 51 to form a nip 52 between the rollers 45.

The outer, peripheral surface of each accelerator roller 45 is slightly resilient and the accelerator rollers 45 are mounted on shafts 53 which are rotatably supported by bearings 54 connected to upper frame members 38. The accelerator rollers 45 are driven by electric motor 55 using a drive belt 56. The electric motor 55 is also supported on the upper frame members 38.

The drive belt 56 is threaded around drive pulleys 57 on the respective roller shafts 53 to cause the accelerator rollers 45 to rotate toward one another. The distance between the outer periphery of each roller 45 at the nip 52 is just slightly smaller than the outer diameter of a shell casing 2. The accelerator rollers 45 rotate at a speed which is sufficiently fast to accelerate a shell casing 2 as it drops through the launch tube 44 and is engaged by the rollers 45 and drawn therebetween. Not all applications will require mechanically accelerating a workpiece through or out of the launch tube 44. However, if the speed at which workpieces 2 pass through the inspection system 1 based solely on acceleration due to gravity is insufficient to keep pace with the rate of production of the workpieces to be inspected, use of mechanical accelerating means such as that described may be preferred.

Once the shell casings 2 are accelerated through the accelerator rollers 45, the shell casings 2 are allowed to fall freely and unsupported through an inspection zone 59. The casing 2 may be described as flying through the inspection zone 59. As used herein, the action of releasing or causing a workpiece or shell casing 2 to fall or fly freely and unsupported or pass unsupported through space may be referred to as launching the workpiece or shell casing regardless of whether the workpiece is dropped or accelerated by means other than gravity (including mechanical, chemical, hydraulic or pneumatic means) and regardless of its trajectory or direction when released.

Figure 9:
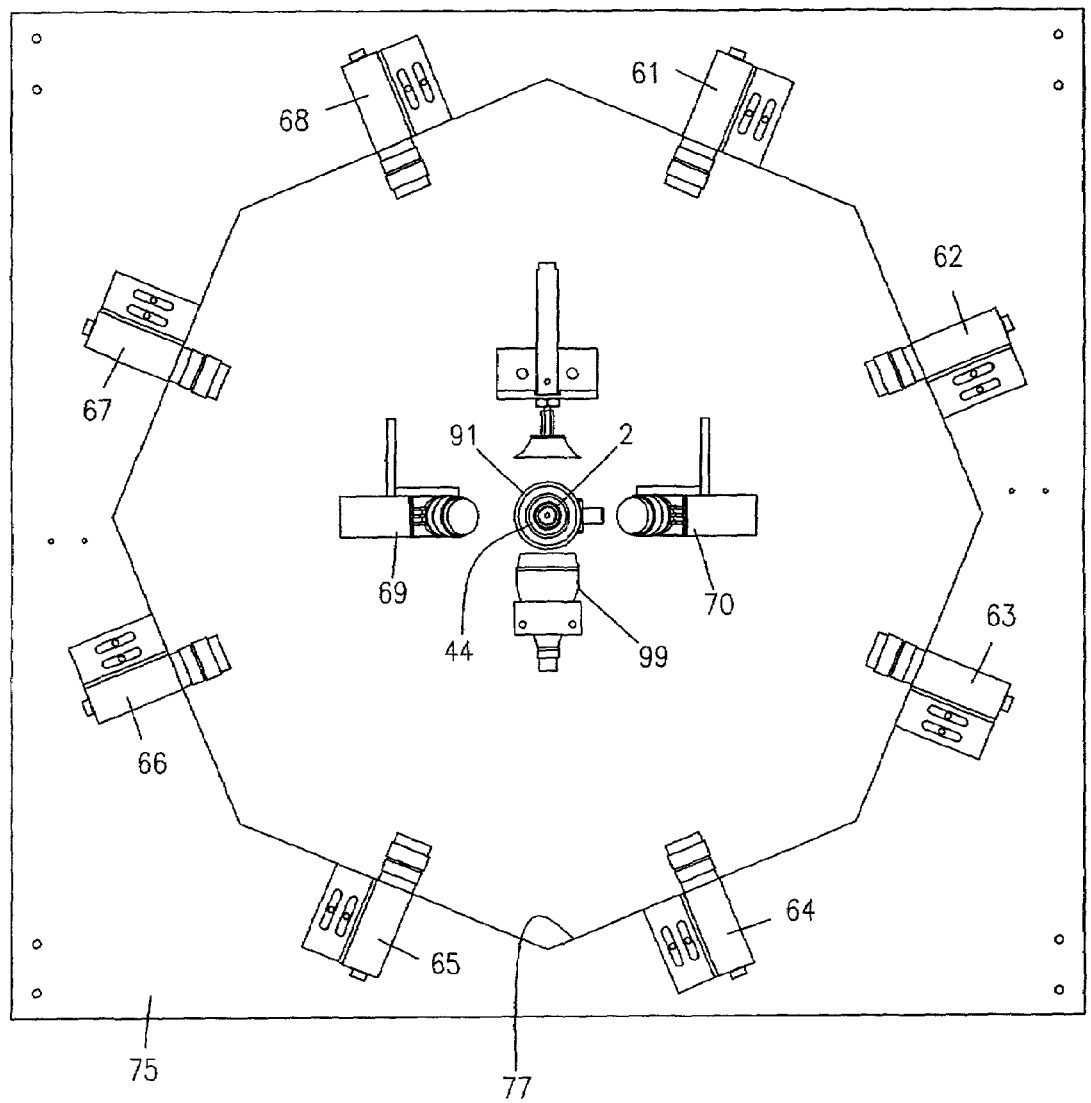
FIG. 9 is an enlarged and fragmentary cross-sectional view taken along line 9—9 of FIG. 2.

The inspection zone 59 comprises a space or zone in which the image capturing assembly 22 is focused to capture one or more images of the workpiece or shell casing 2. As best seen in FIGS. 7 and 9, the image capturing assembly 22 of the embodiment shown, comprises ten cameras 61–70 positioned and focused on the inspection zone 59 which is in the path of travel of a workpiece 2 after it is launched or drops out of the launch tube 44. The cameras 61–70 used may be analog or digital and may also be referred to as a general purpose vision sensor adapted for machine vision systems such as the CVC 1000 camera sold by Cognex Corporation. The inspection zone 59 may also be described as a portion of the path of travel of the workpiece 2 which passes through or within the field of view of the cameras 61–70.

The cameras 61–70 are generally arranged in four groups or sets. A first set of cameras comprises cameras 61, 63, 65 and 67 which are mounted on an annular support ledge 75 ninety degrees apart relative to each other and the inspection zone 59 or path of travel of the workpiece 2. The second set of cameras comprises cameras 62, 64, 66 and 68 which are also mounted on the annular support ledge 75 ninety degrees apart relative to each other and the inspection zone 59 and forty-five degrees apart relative to adjacent cameras 61, 63, 65 or 67. The annular support ledge 75 is connected to the support legs 34 of the frame 14 and includes a large central opening 77 through which the workpiece or casing 2 may fall or pass. The large central opening 77 also presents an unobstructed field of view of the workpiece 2 for the cameras 61–70.

The first and second sets of cameras 61–68 are mounted such that their fields of view extend generally horizontally to focus on the shell casing circumferential wall 13. Cameras 61–68 may be referred to as the circumferential view cameras or shell casing wall cameras. Cameras 61, 63, 65 and 67 are positioned and focused to capture a first set of four different images or a first set of image data (which preferably overlap) of the shell casing circumferential wall 13. Similarly, cameras 62, 64, 66 and 68 are positioned and focused to capture a second set of four different images or a second set of image data (which preferably overlap) of the shell casing circumferential wall 13. The first and second sets of cameras 61–68 are adapted for identifying holes, cracks or other openings in the circumferential wall 13 and determining the size of the opening as discussed in more detail hereafter.

Camera 69 comprises a third camera set and camera 70 comprises a fourth camera set. Referring to FIG. 7, cameras 69 and 70 are mounted on support members 80 and 81 which are connected to intermediate cross frame members 83 which are in turn connected to support legs 34. The cameras 69 and 70 are supported in spaced relation below the inspection zone 59 and on opposite sides of the path of travel of a shell casing 2 as it falls past the inspection zone 59. The cameras 69 and 70 are angled upward to focus on the bottom or base 9 of the a shell casing 2 in the inspection zone 59 to detect the presence or absence of the primer opening 8 in the base 9 as discussed in more detail hereafter.

The first and second sets of cameras 61–68 capture redundant images or image data of the shell casing circumferential wall 13. The redundant sets of images are analyzed separately to enhance the likelihood of correctly identifying a defect in the workpiece. Similarly, cameras 69 and 70 (the third and fourth camera sets) capture redundant images or image data of the shell casing base 9, which are also analyzed separately to enhance the accuracy of the defect identification process.

Referring to FIG. 7, a first position sensor assembly or inspection zone sensor 85, comprising transmitter or emitter 86 and receiver 87, is used to determine when a shell casing 2 has entered into the inspection zone 59. The illustrated transmitter 86 and receiver 87 are mounted to the underside of the annular support ledge 75, in alignment and on opposite sides of the inspection zone 59 and the path of travel of the casing 2 through the inspection zone. The transmitter 86 transmits a beam of light (possibly infrared) through the path of travel of the casing 2 and to receiver 87 which is adapted to detect the presence of a shell casing or workpiece 2 within the inspection zone 59 when the light beam is broken by the passage of a workpiece 2 through the beam.

Referring to FIG. 8, the illumination assembly 20 is adapted to internally illuminate a shell casing 2 in the inspection zone 59. The illumination assembly 20 shown comprises an annular lamp or ring light 90 and a light directing cover or housing 91. The lower section 50 of the launch tube 44 and a lower portion of the collar 49 extend through a central opening 93 in the annular lamp 90. The annular lamp 90 is a ring lamp of the type sold by Schott-Fostec, LLC of Albany, N.Y., including the ringlight part number A08660. The ring light 90 uses fiber optic strands connected to a strobe-type light source not shown to emit light circumferentially around the launch tube 44. The lamp 90 may be referred to as a workpiece illuminator.

The lamp housing 91 fits over the annular lamp 90 and is secured to the underside of the upper support plate 40. A light directing opening 95 is formed in a lower surface of the lamp housing 91 and is positioned in alignment with the opening in the launch tube 44. The light directing opening 95 is sized to permit the shell casings 2 to freely pass therethrough. The size of the light directing opening 95 and distance from the ring light 90 are selected to direct light emitted from the ring light 90 through the mouth 5 of a shell casing 2 when it is in the inspection zone to internally illuminate the shell casing 2 but not to externally illuminate its circumferential wall 13.

Light emitted from the lamp 90 will reflect off of the mouth 5 of the shell casing 2, which when viewed from the perspective of the cameras 61–68 appears as a band or line of relatively bright light. This bright line can be used as a reference or datum within the images captured by the cameras 61–68. The light internally reflected inside of the shell casing 2 will be emitted through any openings in the casing 2 including the primer opening 8 and any unintended openings in the circumferential wall.

Referring to FIGS. 6 and 9, a blower nozzle or vent 99 is mounted to the underside of the upper support plate 40 adjacent and just below the lower end of the launch tube 44 and the ring light 90. Pressurized air is continually supplied to the vent by a supply line (not shown) to blow dust out of the path of the emitted light and the workpiece 2 and out of the inspection zone 59. Dust entrained in the path of the emitted light and in the inspection zone 59 can reflect the emitted light at an angle perceptible by one of the cameras 61–70 which might provide a false indication of a defective part when the image captured by the cameras is analyzed in the manner discussed below.

Referring to FIGS. 2, 7 and 11, a second position sensor assembly or diversion zone sensor 105, comprising transmitter 106 and receiver 107, is used to determine when a shell casing 2 is about to pass across the path of the product diverter 24 within a workpiece diversion zone 108. The transmitter 106 and receiver 107 are mounted or connected to the support members 80 and 81 respectively just below the cameras 69 and 70 and on opposite sides of the path of travel of the casing 2. The transmitter 106 transmits a beam of light through the path of travel of the casing 2 and to receiver 107.

The acceptable product chute 26 is supported by and connected to the frame 14 by lower cross members 110. The acceptable product chute 26 is positioned directly beneath the launch tube 44 in a first path of travel of the workpiece 2 which is straight down. Workpieces which are not identified as having defects are allowed to fall into the acceptable product chute 26. The acceptable product chute 26 preferably feeds the shell casings 2 by gravity to a conveyor (not shown) which conveys the casings 2 to processing equipment which complete the round by inserting a primer in the primer opening 8, filling the casing 2 with gun powder through the mouth 5 and seating a projectile within the neck of the casing 2. It is foreseen that the acceptable product chute 26 could feed the inspected workpieces directly into a box or other storage container or packaging, particularly where the inspection is performed on a completed article of manufacture.

The defective product chute 28 is mounted on the lower cross members 110 on a side of the first path of travel of the workpiece opposite from the product diverter 24. The product diverter 24 is used to divert workpieces identified as having defects out of the first path of travel and into a second path of travel into the defective product chute 28. The defective product chute 28 may direct the defective workpieces into a receptacle or onto a conveyor which might direct the defective workpieces to a recycling system.

The product diverter 24, as best seen in FIGS. 3 and 11, comprises a pneumatically operated linear actuator 115. The product diverter includes a cylinder 116, a plunger or shaft 117 and an abutment member or striker 118. Pressurized air is supplied to the cylinder 116 through hoses (not shown). Valve 121 (see FIG. 3) is used to selectively and alternatingly connect pressurized air to the front and rear of the cylinder 116 to selectively retract and extend the shaft 117. As shown in FIG. 11, extension of the shaft 117, drives the abutment member 118 across the first path of travel of a workpiece 2 to drive or divert a workpiece 2 in front of the abutment member 118 along the second path of travel into the defective product chute 28. The shaft 117 is retracted almost immediately after being extended to retract the abutment member 118 to a retracted position as shown in phantom lines in FIG. 11, out of the path of travel of the next shell casing 2.

A third position sensor assembly or diversion confirmation sensor 125, comprising transmitter 126 and receiver 127 (see FIG. 2), is used to confirm that a workpiece 2 identified as defective has been properly diverted into the defective product chute 28. The transmitter 126 and receiver 127 are mounted on opposed sidewalls 130 and 131 of the defective product chute 28 proximate the opening to the chute 28. The transmitter 126 and receiver 127 extend on opposite sides of the second or diverted path of travel of the casing 2. The transmitter 126 transmits a beam of light through the second path of travel of the casing 2 and to receiver 127.

A fourth position sensor assembly or feed mechanism sensor 135 is shown diagrammatically in FIG. 5. The feed mechanism sensor 135 is mounted in the product feed line 16 to determine whether shell casings 2 are backed up from the accelerator rollers 45 to the sensor 135. This is done to ensure positive feeding by the accelerator rollers 45.

The controller, computer or computer system 30 used is shown diagrammatically in FIG. 5 as a single block. The controller 30 may include a plurality of computers and programmable logic controllers on which one or more computer programs may be run which communicate and operate together to control the operation of the inspection apparatus 1. In the application described herein, the controller 30 may utilize on optical analysis program such as OMI V2.3.1, which is sold by Cognex Corporation, which interfaces with the controller 30 to control operation of the inspection apparatus 1. The controller 30 is connected to or communicates with and receives signals from each of the position sensor assemblies 85, 105, 125 and 135. The controller is also connected to or communicates with the accelerator rollers 45 through the motor 55, the annular lamp 90 (through the strobe type light source), the cameras 61–70 and the product diverter 24 through valve 21. The controller 30 also receives images or image data from each of the cameras 61–70. The image data is processed by the computer program to identify defects in the workpiece 2.

Figure 12:
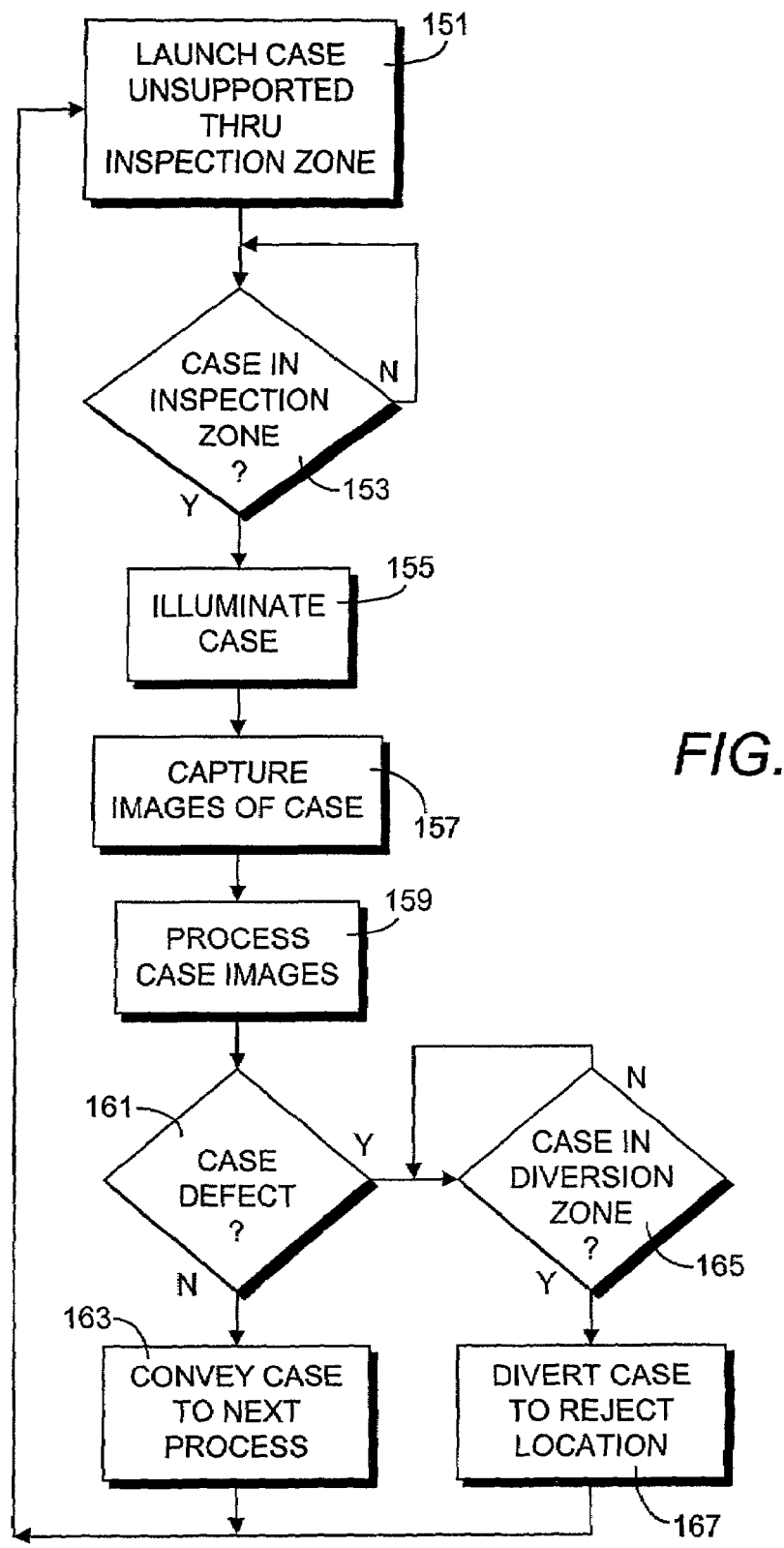
FIG. 12 is a process diagram illustrating some of the steps of the inspection process.

Portions of the inspection process are shown schematically in FIG. 12. The process generally begins with an initial step of feeding shell casings 2 in succession from the feeder (not shown) into the product feed line 16. The shell casings 2 are then fed from the product feed line 16 into the launch tube 44. Each shell casing 2 is allowed to drop under the action of gravity through the launch tube 44 until it reaches the accelerator rollers 45. The controller 30 is programmed to only run the accelerator rollers 45 when the product feed sensor 135 indicates that there are shell casings 2 backed up from the accelerator rollers 45 to the sensor 135.

When running, the accelerator rollers 45 successively engage the shell casings 2 and accelerate them to advance unsupported, out of the lower end of the launch tube 44. The act of consecutively releasing the shell casings 2 to fall unsupported out of the end of the launch tube 44 and into the inspection zone 59, may be referred to as the step of consecutively launching the workpieces to pass unsupported through the inspection zone 59 or past the field of view of the cameras 61–70. The launching step is shown as block 151 in FIG. 12. In the embodiment shown, the shell casings 2 are fed into the product feed line 16 base first so that the mouth 5 of each casing 2 is oriented toward the light source or ring light 90 after the casing 2 exits the launch tube 44.

As the shell casing 2 advances into the inspection zone 59, the base 9 of the shell casing 2 trips the inspection zone sensor 85 at step 153, which sends a signal to the controller 30 indicating a shell casing 2 is in the inspection zone 59. The controller 30 simultaneously causes the ring light 90 to flash on and off at step 155 to internally illuminate the shell casing 2 and at step 157 causes each of the cameras to capture images or image data of the shell casing 2 in the inspection zone 59 while illuminated.

As generally shown in FIG. 8, the distance that the inspection zone 59 is spaced from the lower end of the launch tube 44 and the size of the light directing opening 95 in the light directing housing 91 are selected to result in light L emitted from the ring light 90 to be directed into the shell casing 2 in the inspection zone 59 through its mouth 5. Any rays of light L which are not directed into the shell casing 2 pass by the shell casing 2 at an angle at which they are not perceptible by the cameras 61–70. Some rays of light L from the light source will reflect off of the upper edge of the shell casing forming its mouth 5, at an angle which is perceptible by at least the cameras 61–68 in the form of a band or line of light.

Figure 10:
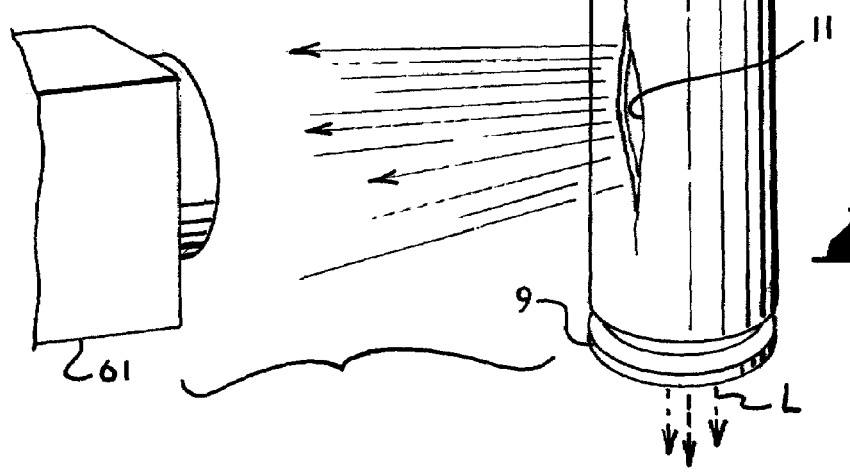
FIG. 10 is a diagrammatic view showing light direct into a shell casing 2 and reflected out of openings therein and being captured by a camera.

The light L directed into the shell casing 2 internally illuminates the shell casing 2 and is internally reflected within the shell casing 2. As generally shown in FIG. 10, the internally reflected light, will be directed out of any openings 11 in the casing circumferential wall 13 and at least a portion of the light L escaping through an opening in the shell casing 2 will be perceptible by any of the cameras 61–68 focused on that area of the shell casing 2. Similarly, light L escaping out of the primer opening 8 in the shell casing base 9 will be perceptible by the cameras 69 and 70. It should be noted that the inspection apparatus 1 may be positioned in a relatively dark room or enclosed by dark panels (not shown) mounted on the frame 14 to increase the relative intensity of any light emitted from the internally illuminated shell casings 2.

The images or image data captured by the cameras 61–70 are arrays of image pixel data and include pixels representing any areas of light emitted from the internally illuminated shell casings 2. This information is communicated to the controller 30 for analysis or processing by the computer program at step 159 to identify defects. The image data from the first set of cameras 61, 63, 65, and 67 is analyzed separate from but simultaneously with the image data from the second set of cameras 62, 64, 66 and 68. Similarly the image data from the third and fourth set of cameras 69 and 70 is analyzed separately and simultaneously. In the application described herein, the images are analyzed to identify areas of contrasting light intensity.

The computer program identifies any areas of more intense light and measures dimensions associated with the area of light. The measurements are then compared to established specifications. When analyzing the image data from the first and second sets of cameras 61–68, image data showing areas of more intense light (other than the light from the mouth 5) in the area which is occupied by the shell casing 2 generally indicate an unwanted opening in the circumferential wall 13 of the shell casing 10. If the dimensions of this area of more intense light exceed established standards, then the computer program processes this information to indicate a defect and a defect signal is generated by the controller 30 at step 161.

When analyzing the image data from cameras 69 and 70 the computer program is looking for an area of more intense light corresponding to the primer opening 8. If such an area of more intense light is not identified or if its dimensions are below established standards, then the computer program processes this information to indicate a defect at step 161 and a defect signal is generated by the controller 30. If the information processed by the computer program does not indicate a defect, the controller may also generate an acceptable product signal. The defect signals and the acceptable product signals may also be referred to as workpiece action signals.

If no defect is identified in the workpiece 2 by the computer program and no defect signal is generated, the workpiece drops past the product diverter 24 and into the acceptable product chute 26 to be conveyed to the next processing station at step 163.

If a defect signal is generated by the controller 30 at step 161, the computer program queries at step 165 whether the diversion zone sensor 105 has been triggered indicating that the shell casing 2 is approaching or has entered the diversion zone 108. When the sensor 105 is triggered to indicate the casing 2 is approaching or in the diversion zone 108 and a defective product signal has been generated for the workpiece 2, the defective product signal is communicated to the product diverter 24 through the valve 121. Under these conditions, the valve 121 is actuated to cause the plunger 117 and striker 118 to rapidly advance across the normal path of travel of the workpiece 2 to strike the just inspected workpiece 2 and divert it into a alternative path which extends into the defective product chute 28 as indicated at step 167 of FIG. 12.

As a workpiece is diverted into the defective product chute 28 it triggers the diversion confirmation sensor 125 which is communicated to the controller 30. If the diversion confirmation sensor 125 is not triggered after a defective shell casing 2 has been detected and before the next shell casing 2 triggers the diversion zone sensor 105, the computer program interprets this information as indicating that the defective casing 2 was not diverted into the defective product chute 128. Under these conditions, the controller 30 is programmed to stop the accelerator rollers 45 to stop further inspections and to signal operators to attempt to remove any casings 2 in or downstream of the acceptable product chute 28 which might have been deemed defective but not directed to the defective product chute 128.

The controller 30 is also programmed to stop the accelerator rollers 45 if the controller 30 determines that two shell casings 2 have been consecutively launched into the inspection zone 69 before the first of the two casings 2 enters the workpiece diversion zone 108. The controller 30 determines that such a condition has occurred if two successively launched casings 2 each trigger the inspection zone sensor 85 prior to the first of the two casings triggering the diversion zone sensor 105. If such a circumstance occurs, corrective action is necessary to ensure that the rate at which the inspection apparatus 1 is operated does not exceed the rate at which it can effectively inspect the workpieces and divert defective product from the acceptable product stream.

Although the inspection apparatus 1 shown and described launches workpieces downward for unobstructed inspection, it is to be understood that unobstructed inspection of a workpiece can be obtained regardless of the direction in which the workpiece is launched. For example, it is foreseen that the launch tube could be curved at a lower end approximately ninety degrees, to launch the workpiece horizontally through a workpiece inspection zone onto which a plurality of cameras are focused.

The number and positioning of the cameras used to obtain the images necessary will depend on numerous factors including the shape of the object inspected, the type and size of defect or characteristic to be detected or analyzed and the degree of accuracy required. For example, obtaining a complete circumferential view of a cylindrical item or workpiece about a single axis, generally requires the use of at least three cameras which preferably are mounted in the same plane, spaced an equal distance from the item to be inspected and an equal distance from each other.

It is also foreseen that modifications to the apparatus and process disclosed may be made depending on the nature of the types of defects or product characteristics to be identified or measured, the nature of the workpiece and other factors. For example, if the inspection process is to be used to inspect an outer surface of a workpiece for dents, dings, discoloration, or critical dimensions of the workpiece, different types of lights would be used to illuminate the outer surface of the workpiece and the lights would be positioned in different locations.

It is also foreseen that the inspection apparatus and process disclosed could be modified for use in sorting items. If for example, similar items of different lengths were to be sorted by their length, lights would probably be selected and positioned to externally illuminate each workpiece in the inspection zone and the computer program would be adapted to determine the length of each workpiece and compare its against a standard length (or range of lengths) for each class into which the workpiece is to be sorted based on length. Additional diverters or different types of diverters might then be used in cooperation with the computer program to permit the system to separate the workpieces in more than just two classificiations.

It is also to be understood that although various sensors are described as being used to determine the position of the workpiece during the process, the computer program could rely on timing to anticipate when the casing 2 will advance to the inspection zone 59 or the diversion zone 108 and cause the cameras, illumination system or diverting system to act on the workpiece at the desired moment.

Instead of using a diverter to automatically divert defective product out of the product stream for acceptable goods, it is to be understood that other means could be utilized to divert or remove defective product from the product stream. For example, it is foreseen that detection of a defective workpiece could cause the controller 30 to stop the accelerator rollers 45 and send a signal to an operator instructing them or indicating the need to manually inspect and if necessary manually remove the workpiece which was identified as defective. It is also foreseen that the apparatus could be modified to simply mark items in the product stream to indicate whether or not the item meets established criteria as analyzed by the computer 30. Further the diverter may take numerous forms including possibly a magnet selectively energized to change the path of a metal item identified as defective. The diverter could be a blower selectively directing air into the path of an item identified as defective (or otherwise selected) to cause it to change paths.

Although the application described utilized visible light to identify defects, it is to be understood that cameras or light detecting devices which detect light from other wavelengths of the electromagnetic radiation spectrum could be used to detect defects in workpieces or otherwise characterize the workpieces. For example cameras or light detecting devices adapted to capture images of infrared light could be utilized along with or without a separate infrared light source. In addition to any conventional definition of the term camera, as used herein the term camera is intended to include any device adapted to capture images and convert the image into electrical impulses, signals, charge patterns or data. The term images is generally intended to include any pattern of light, whether visible or not, associated with an object.

As used in the claims, any reference to analyzing captured images or image data to determine if the captured images or image data indicate the presence of a selected characteristic of a workpiece may also include determining if the captured images or image data indicate the absence of a selected characteristic.

It is to be understood that while certain forms of the present invention have been illustrated and described herein, it is not to be limited to the specific forms or arrangement of parts and process steps described and shown.

What is claimed and desired to be secured by Letters Patent is as follows:

1. A workpiece inspection system for consecutively inspecting a plurality of workpieces, each workpiece including at least a first opening and said system being adapted to determine a presence of additional openings in said workpiece, said system comprising:
    a) a camera positioned to capture an image of a workpiece in an inspection zone;
    b) a launching device from which the workpieces may be consecutively launched to pass unsupported through said inspection zone;
    c) a sensor positioned to sense when a workpiece has entered said inspection zone;
    d) a light positioned to direct light into a workpiece when the workpiece is located in said inspection zone; and
    e) a controller communicating with said sensor and said camera and programmed to cause said camera to capture an image of the workpiece when said sensor senses the workpiece has entered said inspection zone; said controller programmed to analyze said image of the workpiece captured by the camera to identify any defects in the workpiece, including the presence of additional openings in the workpiece.

2. The workpiece inspection apparatus as in claim 1 further comprising a diverter selectively operable to divert a workpiece from a first path of travel to a second path of travel after the workpiece passes through the field of view of the camera; said diverter communicating with said controller and said controller programmed to cause said diverter to divert to said second path of travel any work piece in which a defect has been identified by said controller.

3. A workpiece inspection system for consecutively inspecting a plurality of hollow workpieces, each workpiece including at least a first opening and said workpiece inspection system adapted to determine the presence of additional openings in said workpiece; said workpiece inspection system comprising:
    a) a plurality of cameras each positioned to capture image data of a workpiece in an inspection zone;
    b) a launch tube from which the workpieces may be consecutively launched to pass unsupported through said inspection zone;
    c) a light positioned to direct light into a workpiece through the first opening when the workpiece is located in said inspection zone; and
    d) a controller causing each of said cameras to capture an image of the workpiece when the workpiece has entered said inspection zone; said controller programmed to analyze the images of the workpiece captured by the cameras to determine the presence of any additional openings in the workpiece.

4. The workpiece inspection system as in claim 3 wherein said light comprises a ring light secured around said launch tube.

5. The workpiece inspection system as in claim 3 wherein said controller is further programmed to analyze the images of the workpiece captured by the cameras to determine the relative size of any additional openings in the workpiece and determine if the size of each additional opening complies with an established acceptable size for additional openings.

6. The workpiece inspection system as in claim 3 comprising a diverter selectively operable to divert a workpiece from a first path of travel to a second path of travel after the workpiece passes through said inspection zone; said diverter communicating with said controller and said controller programmed to cause said diverter to divert to said second path of travel any workpiece identified by said controller as having an additional opening whose size does not comply with the established acceptable size for additional openings.

7. A process for inspecting a succession of workpieces wherein each workpiece is hollow and includes a first opening and the workpieces are inspected to detect an additional opening, the process comprising the steps of:
    a) positioning a camera to define a workpiece inspection zone and to capture an image of a workpiece within said workpiece inspection zone;
    b) successively launching workplaces unsupported through said inspection zone;
    c) capturing a respective image of each workpiece launched through said inspection zone;
    d) internally illuminating each workpiece through the first opening simultaneously with the step of capturing the image of the workpiece with the camera and in response to sensing the workpiece passing within the field of view of the camera; and
    e) processing each image by a computer to detect the presence of a selected characteristic in the respective workpiece from the image including an additional opening in said workpiece.

8. The workpiece inspection system as in claim 7 further comprising the step of:
    a) differentiating the workpieces for which the presence of the selected characteristic has been detected from the workpieces for which the presence of the selected characteristic has not been detected.

9. The workpiece inspection system as in claim 7 further comprising the step of:
    a) directing the workpieces for which the presence of the selected characteristic has been detected to a first area and directing the workpieces for which the presence of the selected characteristic has not been detected to a second area.

10. A process for inspecting a plurality of workpieces wherein the workpieces are hollow and include a first opening and the workpieces are inspected to detect additional openings; the process comprising the steps of:
   a) consecutively launching the workpieces to pass unsupported past a field of view of a camera;
   b) sensing when each workpiece passes within the field of view of the camera,
   c) upon sensing each workpiece passing within the field of view of the camera, capturing image data of the workpiece with the camera, and including the step of:
      1) internally illuminating each workpiece through the first opening simultaneously with the step of capturing the image of the workpiece with the camera and in response to sensing the workpiece passing within the field of view of the camera;
   d) analyzing the captured image data to determine if the captured image data indicates the presence of a selected characteristic of said workpiece;
   e) upon determining that the captured image of a workpiece does not indicate unacceptable defects in the workpiece, directing the workpiece to a first area; and
   f) upon determining that the captured image of a workpiece does indicate unacceptable defects in the workpiece, directing the workpiece to a second area.

11. The process as in claim 10 wherein said workpieces are inspected to detect additional openings which are larger than a specified opening wherein the step of analyzing the captured image comprises measuring the size of areas in the captured images in which the intensity of the light exceeds a specified intensity and comparing the measured size versus a minimum acceptable size.

12. The process as in claim 10 wherein the camera comprises one of a plurality of cameras.

13. The process as in claim 10 wherein the step of launching the workpieces past the field of view of a camera comprises dropping the workpiece past the field of view of the camera.

14. The process as in claim 10 wherein the step of launching the workpiece past the field of view a camera comprises accelerating each workpiece downward and releasing the workpiece to drop past the field of view of the camera.

15. A process for inspecting a plurality of workpieces wherein the workpieces are hollow and include a first opening and the workpieces are inspected to detect additional openings; the process comprising the steps of
   a) consecutively launching the workpieces to pass unsupported past a field of view of each of a plurality of cameras, each camera positioned and focused to record a different view of each workpiece as it passes within the field of view of the camera;
   b) sensing when each workpiece passes within the field of view of the cameras;
   c) upon sensing each workpiece passing within the fields of view of the cameras, simultaneously illuminating the workpiece and causing each camera to capture an image of the workpiece, and including the step of:
      1) internally illuminating each workpiece through the first opening simultaneously with the step of capturing the image of the workpiece with the camera and in response to sensing the workpiece passing within the field of view of the cameras;
   d) analyzing the captured images of each workpiece to determine if the images indicates unacceptable defects in the workpiece;
   e) upon determining that the captured images of a workpiece do not indicate unacceptable defects in the workpiece directing the workpiece to a first area; and
   f) upon determining that the captured images of a workpiece do indicate unacceptable defects in the workplace, directing the workpiece to a second area.

16. The process as in claim 15 wherein said workpieces are inspected to detect additional openings which are larger than a specified opening wherein the step of analyzing the captured images comprises measuring the size of areas in the captured images in which the intensity of the light exceeds a specified intensity and comparing the measured size versus a minimum acceptable size.

17. The process as in claim 15 wherein the step of launching the workpieces past the field of view of the cameras comprises dropping the workpiece past the field of view of the cameras.

18. The process as in claim 15 wherein the step of launching the workpiece past the field of view the cameras comprises accelerating each workpiece downward and releasing the workpiece to drop past the field of view of the cameras.

* * * * *